United States Patent
Ford et al.

(10) Patent No.: US 11,627,713 B1
(45) Date of Patent: Apr. 18, 2023

(54) MAIZE HYBRID VARIETY ICH19849

(71) Applicant: INARI AGRICULTURE TECHNOLOGY, INC., Cambridge, MA (US)

(72) Inventors: Eric James Ford, Syracuse, NE (US); Ryan Edward Frazier, Omaha, NE (US); Scott Clarence Stelpflug, West Lafayette, IN (US)

(73) Assignee: Inari Agriculture Technology, Inc., Cambridge, MA (US)

( * ) Notice: Subject to any disclaimer, the term of this patent is extended or adjusted under 35 U.S.C. 154(b) by 241 days.

(21) Appl. No.: 17/143,662

(22) Filed: Jan. 7, 2021

Related U.S. Application Data

(60) Provisional application No. 63/004,099, filed on Apr. 2, 2020.

(51) Int. Cl.
*A01H 5/10* (2018.01)
*A01H 6/46* (2018.01)

(52) U.S. Cl.
CPC .............. *A01H 6/4684* (2018.05); *A01H 5/10* (2013.01)

(58) Field of Classification Search
CPC .................................................... A01H 6/4684
USPC ............................................................ 800/275
See application file for complete search history.

(56) References Cited

U.S. PATENT DOCUMENTS

| | | | |
|---|---|---|---|
| 5,276,263 A | 1/1994 | Foley | |
| 5,416,261 A | 5/1995 | Miller | |
| 5,563,325 A | 10/1996 | Morrow | |
| 6,677,509 B2 | 1/2004 | Brown | |
| 9,675,025 B1 * | 6/2017 | Bing | .................... A01H 6/4684 |

OTHER PUBLICATIONS

Kaeppler et al, Plant Molecular Biology, 43:179-188 (Year: 2000).*
Stroud et al, eLife, 2:e00354 (Year: 2013).*
Kaeppler et al., "Epigenetic aspects of somaclonal variation in plants," Plant Molecular Biology, Jun. 2000, vol. 43, pp. 179-188.

* cited by examiner

*Primary Examiner* — Li Zheng
(74) *Attorney, Agent, or Firm* — McKee, Voorhees & Sease PLC

(57) ABSTRACT

Disclosed herein are seed and plants of the maize hybrid variety designated ICH19849, as well as cells and cell cultures derived therefrom. Further disclosed are methods for producing seed, commodity products, and derived progeny plants from the maize hybrid variety designated ICH19849.

17 Claims, No Drawings

MAIZE HYBRID VARIETY ICH19849

CROSS-REFERENCE TO RELATED APPLICATIONS

This U.S. non-provisional patent application claims the benefit of U.S. Provisional Patent Application No. 63/004,099, filed Apr. 2, 2020.

FIELD

Aspects of this disclosure relate generally to the field of maize breeding, in particular to seed and plants of the maize hybrid variety designated ICH19849, representative seed of which having been deposited under ATCC Accession number PTA-126949. Further aspects of the disclosure relate to plant cells, plant parts, tissue cultures, and plants produced from the seed of the maize hybrid variety ICH19849. Still further aspects of the disclosure relate to progeny, variants, mutants, and minor modifications of the maize hybrid variety ICH19849. Additional aspects of this disclosure are related to methods for producing maize plants comprising crossing the maize hybrid variety ICH19849 with itself or with another maize plant, as well as methods for producing a maize plant characterized by one or more specific traits introduced or introgressed into the maize hybrid variety ICH19849 (e.g., by backcross conversion, transformation, genome editing, and/or epigenetic modification).

BACKGROUND

It is the goal of maize breeders to combine multiple desirable traits (e.g., improvements in yield, pest or disease resistance, tolerance to abiotic stress, nutritional qualities, and agronomic qualities) in a single maize inbred or hybrid variety. To create an inbred maize variety, breeders self-pollinate maize plants, evaluate the resulting progeny, and select for the desired phenotype, repeating this process over many generations in order to produce an inbred maize line that is highly homozygous (homozygous at many or almost all gene loci) and that produces uniform progeny. Crossing two different inbred maize parents produces first generation ("$F_1$") hybrid maize plants that are heterozygous at many gene loci, phenotypically uniform, and often superior in performance in comparison to one or both inbred parents. Maize breeders aim to develop both superior inbred parent maize lines as well as superior maize hybrid varieties based on crosses of inbred maize lines.

SUMMARY

Disclosed herein are novel maize hybrid varieties, including the maize variety designated ICH19849, representative seed of which having been deposited under ATCC Accession number PTA-126949.

Each of the novel maize hybrid varieties described in this disclosure can be arrived at through crossing of inbred parent maize lines or through selection of the desirable characteristics (e.g., as detailed in Table 1 of this disclosure) by using any breeding and selection method deemed appropriate by the maize breeder. In embodiments, the maize hybrid variety ICH19849 is made by crossing female parent inbred line RR728-18 (ATCC Accession number PTA-5628; disclosed in U.S. Pat. No. 6,677,509, which is incorporated herein by reference in its entirety) with male parent line LH185 (ATCC Accession number 75618, disclosed in U.S. Pat. No. 5,416,261, which is incorporated herein by reference in its entirety) as detailed below. Further embodiments include a maize plant having essentially all the physiological and morphological characteristics of the maize hybrid variety ICH19849, and further characterized by having at least one additional trait, e.g., an agronomically or economically useful trait such as increased tolerance of biotic or abiotic stress, resistance to herbicides commonly used in commercial production of maize, male sterility, and modified nutritional content.

Other aspects of this disclosure are related to seeds, plant parts, tissues, callus, and tissue cultures of the maize hybrid variety ICH19849, maize plantlets or plants regenerated or grown therefrom, and progeny plants and seeds derived from these or directly from the maize hybrid variety ICH19849. Additional aspects of this disclosure are related to methods of producing a maize plant derived from the maize hybrid variety ICH19849, for example by backcrossing, genetic transformation to introduce a transgene, or editing of the genome at a predetermined location with a sequence-specific nuclease. Yet other aspects of the disclosure are related to seed of the maize hybrid variety ICH19849 or of their progeny or derived plants, and commodity products produced from these seeds or from the plants themselves. Also disclosed are methods of producing nucleic acid preparations from the seed or a maize plant of the maize hybrid variety ICH19849 or of their progeny or derived plants, obtaining genomic or genetic information from the nucleic acid preparations, and using the information thus obtained in maize breeding.

DETAILED DESCRIPTION OF THE INVENTION

Definitions of Plant Characteristics

Barren Plants: Plants that are barren, i.e., lack an ear with grain, or have an ear with only a few scattered kernels.

Cg: Colletotrichum graminicola rating. The rating multiplied by 10 is approximately equal to percent total plant infection.

CLN: Maize Lethal Necrosis (combination of Maize Chlorotic Mottle Virus and Maize Dwarf Mosaic virus) rating. A numerical rating that is based on a 1 to 9 scale of severity in which "1" indicates "most resistant" and "9" indicates "most susceptible".

Cn: *Corynebacterium nebraskense* rating. The rating multiplied by 10 is approximately equal to percent total plant infection.

Cz: *Cercospora zeae-maydis* rating. The rating multiplied by 10 is approximately equal to percent total plant infection.

Dgg: *Diatraea grandiosella* girdling rating. A rating in which the value equals percent plants girdled and stalk lodged.

Dropped Ears: Ears that have fallen from the plant to the ground.

Dsp: *Diabrotica* species root rating. A rating that is based on a 1 to 9 scale in which "1" indicates "least affected" and "9" indicates "severe pruning".

Ear-Attitude: The attitude or position of the ear at harvest, which is scored as upright, horizontal, or pendant.

Ear-Cob Color: The color of the cob, which is scored as white, pink, red, or brown.

Ear-Cob Diameter: The average diameter of the cob when measured at the midpoint.

Ear-Cob Strength: A measure of mechanical strength of the cobs to breakage, which is scored as strong or weak.

Ear-Diameter: The average diameter of the ear when measured at the midpoint.

Ear-Dry Husk Color: The color of the husks at harvest, which is scored as buff, red, or purple.

Ear-Fresh Husk Color: The color of the husks 1 to 2 weeks after pollination, which is scored as green, red, or purple.

Ear-Husk Bract: The length of an average husk leaf, which is scored as short, medium, or long.

Ear-Husk Cover: The average distance from the tip of the ear to the tip of the husks in which the minimum value is no less than zero.

Ear-Husk Opening: An evaluation of husk tightness at harvest, which is scored as tight, intermediate, or open.

Ear-Length: The average length of the ear.

Ear-Number Per Stalk: The average number of ears per plant.

Ear-Shank Internodes: The average number of internodes on the ear shank.

Ear-Shank Length: The average length of the ear shank.

Ear-Shelling Percent: The average of the shelled grain weight divided by the sum of the shelled grain weight and cob weight for a single ear.

Ear-Silk Color: The color of the silk observed 2 to 3 days after silk emergence, which is scored as green-yellow, yellow, pink, red, or purple.

Ear-Taper (Shape): The taper or shape of the ear, which is scored as conical, semi-conical, or cylindrical.

Ear-Weight: The average weight of an ear.

Early Stand: The percent of plants that emerge from the ground as determined in the early spring.

ER: Ear rot rating. A rating in which the value approximates percent ear rotted.

Final Stand Count: The number of plants just prior to harvest.

GDUs: Growing degree units. GDUs are calculated by the Barger Method in which the heat units for a 24-hour period are calculated as follows: [(Maximum daily temperature+Minimum daily temperature)/2]−50. The highest maximum daily temperature used is 86 degrees Fahrenheit. and the lowest minimum temperature used is 50 degrees Fahrenheit.

GDUs to Shed: The number of growing degree units (GDUs) or heat units required for a variety to have approximately 50% of the plants shedding pollen as measured from time of planting. GDUs to shed is determined by summing the individual GDU daily values from the planting date to the date of 50% pollen shed.

GDUs to Silk: The number of growing degree units (GDUs) for a variety to have approximately 50% of the plants with silk emergence as measured from the time of planting. GDUs to silk is determined by summing the individual GDU daily values from the planting date to the date of 50% silking.

Hc2: *Helminthosporium carbonum* race 2 rating. The rating multiplied by 10 is approximately equal to percent total plant infection.

Hc3: *Helminthosporium carbonum* race 3 rating. The rating multiplied by 10 is approximately equal to percent total plant infection.

Hm: *Helminthosporium maydis* race 0 rating. The rating multiplied by 10 is approximately equal to percent total plant infection.

Ht1: *Helminthosporium turcicum* race 1 rating. The rating multiplied by 10 is approximately equal to percent total plant infection.

Ht2: *Helminthosporium turcicum* race 2 rating. The rating multiplied by 10 is approximately equal to percent total plant infection.

HtG: Chlorotic-lesion type resistance. "+" indicates the presence of Ht chlorotic-lesion type resistance; "−"indicates absence of Ht chlorotic-lesion type resistance; and "+/−" indicates segregation of Ht chlorotic-lesion type resistance. The rating multiplied by 10 is approximately equal to percent total plant infection.

Kernel-Aleurone Color: The color of the aleurone, which is scored as white, pink, tan, brown, bronze, red, purple, pale purple, colorless, or variegated.

Kernel-Cap Color: The color of the kernel cap observed at dry stage, which is scored as white, lemon-yellow, yellow, or orange.

Kernel-Endosperm Color: The color of the endosperm, which is scored as white, pale yellow, or yellow.

Kernel-Endosperm Type: The type of endosperm, which is scored as normal, waxy, or opaque.

Kernel-Grade: The percent of kernels that are classified as rounds.

Kernel-Length: The average distance from the cap of the kernel to the pedicel.

Kernel-Number Per Row: The average number of kernels in a single row.

Kernel-Pericarp Color: The color of the pericarp, which is scored as colorless, red-white crown, tan, bronze, brown, light red, cherry red, or variegated.

Kernel-Row Direction: The direction of the kernel rows on the ear, which is scored as straight, slightly curved, spiral, or indistinct (scattered).

Kernel-Row Number: The average number of rows of kernels on a single ear.

Kernel-Side Color: The color of the kernel side observed at the dry stage, which is scored as white, pale yellow, yellow, orange, red, or brown.

Kernel-Thickness: The distance across the narrow side of the kernel.

Kernel-Type: The type of kernel, which is scored as dent, flint, or intermediate.

Kernel-Weight: The average weight of a predetermined number of kernels.

Kernel-Width: The distance across the flat side of the kernel.

Kz: *Kabatiella zeae* rating. The rating multiplied by 10 is approximately equal to percent total plant infection.

Leaf-Angle: Angle of the upper leaves to the stalk, which is scored as upright (0 to 30 degrees), intermediate (30 to 60 degrees), or lax (60 to 90 degrees).

Leaf-Color: The color of the leaves 1 to 2 weeks after pollination, which is scored as light green, medium green, dark green, or very dark green.

Leaf-Length: The average length of the primary ear leaf.

Leaf-Longitudinal Creases: A rating of the number of longitudinal creases on the leaf surface 1 to 2 weeks after pollination. Creases are scored as absent, few, or many.

Leaf-Marginal Waves: A rating of the waviness of the leaf margin 1 to 2 weeks after pollination, which is rated as none, few, or many.

Leaf-Number: The average number of leaves of a mature plant. Counting begins with the cotyledonary leaf and ends with the flag leaf Leaf-Sheath Anthocyanin: A rating of the level of anthocyanin in the leaf sheath 1 to 2 weeks after pollination, which is scored as absent, basal-weak, basal-strong, weak, or strong.

Leaf-Sheath Pubescence: A rating of the pubescence of the leaf sheath. Ratings are taken 1 to 2 weeks after pollination and scored as light, medium, or heavy.

Leaf-Width: The average width of the primary ear leaf when measured at its widest point.

LSS: Late season standability. The value multiplied by 10 is approximately equal to percent plants lodged in disease evaluation plots.

Moisture: The moisture of the grain at harvest.

On1: *Ostrinia nubilalis* 1st brood rating. The rating is based on a 1 to 9 scale in which "1" indicates "resistant" and "9" indicates "susceptible".

On2: *Ostrinia nubilalis* 2nd brood rating. The rating is based on a 1 to 9 scale in which "1" indicates "resistant" and "9" indicates "susceptible".

Relative Maturity: A maturity rating based on regression analysis. The regression analysis is developed by utilizing check hybrids and their previously established day rating versus actual harvest moistures. Harvest moisture on the hybrid in question is determined and that moisture value is inserted into the regression equation to yield a relative maturity.

Root Lodging: Root lodging is the percentage of plants that root lodge. A plant is counted as root lodged if a portion of the plant leans from the vertical axis by approximately 30 degrees or more.

Seedling Color: Color of leaves at the 6 to 8 leaf stage.

Seedling Height: Plant height at the 6 to 8 leaf stage.

Seedling Vigor: A visual rating of the amount of vegetative growth on a 1 to 9 scale in which the best and worst ratings are "1" and "9", respectively. The score is taken when the average entry in a trial is at the fifth leaf stage.

Selection Index: The selection index gives a single measure of hybrid's worth based on information from multiple traits. One of the traits that is almost always included is yield. Traits may be weighted according to the level of importance assigned to them.

Sr: *Sphacelotheca reiliana* rating. The rating is actual percent infection.

Stalk-Anthocyanin: A rating of the amount of anthocyanin pigmentation in the stalk. The stalk is rated 1 to 2 weeks after pollination as absent, basal-weak, basal-strong, weak, or strong.

Stalk-Brace Root Color: The color of the brace roots observed 1 to 2 weeks after pollination as green, red, or purple.

Stalk-Diameter: The average diameter of the lowest visible internode of the stalk.

Stalk-Ear Height: The average height of the ear when measured from the ground to the point of attachment of the ear shank of the top developed ear to the stalk.

Stalk-Internode Direction: The direction of the stalk internode observed after pollination as straight or zigzag.

Stalk-Internode Length: The average length of the internode above the primary ear.

Stalk Lodging: The percentage of plants that did stalk lodge. Plants are counted as stalk lodged if the plant is broken over or off below the ear.

Stalk-Nodes With Brace Roots: The average number of nodes having brace roots per plant.

Stalk-Plant Height: The average height of the plant when measured from the soil to the tip of the tassel.

Stalk-Tillers: The percent of plants that have tillers. A tiller is defined as a secondary shoot that has developed as a tassel capable of shedding pollen.

Staygreen: Staygreen is a measure of general plant health near the time of black layer formation (physiological maturity) and is usually recorded at the time the ear husks of most entries within a trial have turned a mature color. Scoring is on a 1 to 9 basis in which "1" and "9" are the best and worst score, respectively.

STR: Stalk rot rating. The rating is based on a 1 to 9 scale of severity in which "1" indicates "25% of inoculated internode rotted" and "9" indicates "entire stalk rotted and collapsed".

SVC: Southeastern Virus Complex (combination of Maize Chlorotic Dwarf Virus and Maize Dwarf Mosaic Virus) rating. The numerical rating is based on a 1 to 9 scale of severity in which "1" indicates "most resistant" and "9" indicates "most susceptible".

Tassel-Anther Color: The color of the anthers at 50% pollen shed, which is scored as green-yellow, yellow, pink, red, or purple.

Tassel-Attitude: The attitude of the tassel after pollination, which is scored as open or compact.

Tassel-Branch Angle: The angle of an average tassel branch to the main stem of the tassel, which is scored as upright (less than 30 degrees), intermediate (30 to 45 degrees), or lax (greater than 45 degrees).

Tassel-Branch Number: The average number of primary tassel branches.

Tassel-Glume Band: The closed anthocyanin band at the base of the glume, which is scored as present or absent.

Tassel-Glume Color: The color of the glumes at 50% shed, which is scored as green, red, or purple.

Tassel-Length: The length of the tassel, which is measured from the base of the bottom tassel branch to the tassel tip.

Tassel-Peduncle Length: The average length of the tassel peduncle, which is measured from the base of the flag leaf to the base of the bottom tassel branch.

Tassel-Pollen Shed: A visual rating of pollen shed that is determined by tapping the tassel and observing the pollen flow of approximately five plants per entry. The rating is based on a 1 to 9 scale in which "9" indicates "sterile" and "1" indicates "most pollen".

Tassel-Spike Length: The length of the spike, which is measured from the base of the top tassel branch to the tassel tip.

Test Weight: Weight of the grain in pounds for a given volume (bushel) adjusted to 15.5% moisture.

Yield: Yield of grain at harvest adjusted to 15.5% moisture.

Other Definitions

Allele: Any of one or more alternative forms of a gene locus, all of which relate to one trait or characteristic. In a diploid cell or organism, the two alleles of a given gene occupy corresponding loci on a pair of homologous chromosomes.

Backcrossing: A process in which a breeder repeatedly crosses hybrid progeny back to one of the parents, for example, a first generation hybrid ($F_1$) with one of the parental genotypes of the $F_1$ hybrid.

Crossing: The pollination of a female flower of a maize plant, thereby resulting in the production of seed from the flower.

Cross-pollination: Fertilization by the union of two gametes from different plants.

Diploid: A cell or organism having two sets of chromosomes.

Emasculate: The removal of plant male sex organs or the inactivation of the organs with a chemical agent or a cytoplasmic or nuclear genetic factor conferring male sterility.

$F_1$ Hybrid: The first generation progeny of the cross of two plants.

Genetic Complement: An aggregate of nucleotide sequences, the expression of which sequences defines the phenotype in maize plants, or components of plants including cells or tissue.

Genotype: The genetic constitution of a cell or organism.

Haploid: A cell or organism having one set of the two sets of chromosomes in a diploid.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Genetic loci that contribute, at least in part, certain numerically representable traits that are usually continuously distributed.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing wherein essentially all the morphological and physiological characteristics of an inbred are recovered in addition to the characteristics conferred by the single locus transferred into the inbred via the backcrossing technique. Exemplary procedures for the preparation of such single locus conversions are disclosed in U.S. Pat. No. 7,205,460, the entire disclosure of which is specifically incorporated herein by reference. A single locus may comprise one gene, or in the case of transgenic plants, one or more transgenes integrated into the host genome at a single site (locus). By "essentially all the morphological and physiological characteristics", it is meant that all the characteristics of a plant are recovered that are otherwise present when compared in the same growing conditions or environment, other than an occasional variant trait that might arise during backcrossing or direct introduction of a transgene.

Tissue Culture: A composition comprising isolated cells of the same or a different type or a collection of such cells organized into parts of a plant.

Transgene: A genetic sequence which has been introduced into the nuclear or chloroplast genome of a maize plant by a genetic transformation technique, resulting in a heterologous insertion in the transformed genome. Transgenes can include genetic sequence from an organism other than *Zea mays* or another *Zea* species, or can be "cisgenic", that is to say, obtained from a *Zea mays* genome.

Variety Descriptions

Variety ICH19849

Disclosed herein is a novel maize hybrid variety designated ICH19849. Maize hybrid variety ICH19849 was produced from a cross of two inbred maize lines, designated "female inbred variety 1" (RR728-18; ATCC Accession number PTA-5628) and "male inbred variety 1" (LH185; ATCC Accession number 75618). The morphological characteristics of the maize hybrid variety ICH19849 and of the parent lines are presented in Table 1. Also provided in Table 1 are the morphological characteristics of a comparable maize hybrid LH195/LH216, grown under the same conditions.

TABLE 1*

|  | Female Inbred Variety 1 (ATCC Accession number PTA-5628) | Male Inbred Variety 1 (ATCC Accession number 75618) | Hybrid Variety ICH19849 | LH195/ LH216 |
|---|---|---|---|---|
| STALK | | | | |
| Plant Height (cm) | 186 | 163 | 299 | 295 |
| Ear height (cm) | 86 | 35 | 121 | 120 |
| Anthocyanin | N/A | Absent | absent | moderate |
| Brace root color | N/A | Green | faint | variegated |
| Internode direction | Straight | Straight | straight | straight |
| Internode length (cm) | 12.2 | 13 | 22.7 | 24 |
| LEAF | | | | |
| Leaf color | Dark green | Medium green | Dark green | Medium green |
| Leaf length (cm) | 86.4 | 59 | 80 | 84 |
| Leaf width (cm) | 11 | 8 | 9 | 11 |
| Sheath anthocyanin | N/A | Absent | absent | moderate |
| Sheath pubescence | Moderate | Light | light | light |
| Marginal waves | Few | Few | moderate | few |
| Longitudinal creases | Few | Few | few | few |
| TASSEL | | | | |
| Tassel length (cm) | 48 | 40 | 45 | 55 |
| Peduncle length (cm) | 18 | 3 | 10.5 | 10 |
| Branch number | 7.3 | 4 | 8 | 8 |
| Anther color | Light green | yellow | Light green | yellow |
| Glume color | Light Green | Green | Light green | Green with brown margin |
| Glume band | Absent | Absent | absent | absent |
| EAR | | | | |
| Number of ears per stalk | 1 | 1 | 1 | 1 |
| Ear position | upright | pendent | pendent | pendent |
| Ear shape | Semi-conical | Semi-conical | Semi-conical | Semi-conical |
| Ear length (cm) | 14 | 12 | 16 | 20 |
| Ear diameter (cm) | 4.2 | 3.5 | 4.7 | 4 |
| Shank length (cm) | 10.4 | 5 | 6.4 | 6 |
| Silk color | Light Green | Green | Light green | Light green |
| Husk bract | n/a | n/a | n/a | n/a |
| Husk cover (cm) | 4 | 5 | 4 | 6 |
| Husk opening | Tight | intermediate | Tight | Very tight |
| Husk color, fresh | Light Green | Green | green | green |
| Husk color, dry | Buff | Buff | buff | buff |
| Cob diameter (cm) | 2.5 | 2.5 | 2.5 | 2.2 |
| Cob color | Red | White | Pink | pink |
| Shelling percent | n/a | n/a | n/a | n/a |
| KERNEL | | | | |
| Kernel row number | 15.4 | 10 | 16.5 | 14 |
| Kernel number per row | 31 | 20 | 35 | 40 |
| Row direction | Scattered | Straight | straight | straight |
| Type | Dent | dent | dent | dent |
| Kernel cap color | Yellow | yellow | yellow | yellow |
| Kernel side color | Yellow | yellow | yellow | yellow |
| Kernel length | 10 | 11 | 12 | 11 |

TABLE 1*-continued

| | Female Inbred Variety 1 (ATCC Accession number PTA-5628) | Male Inbred Variety 1 (ATCC Accession number 75618) | Hybrid Variety ICH19849 | LH195/ LH216 |
|---|---|---|---|---|
| (depth) (mm) | | | | |
| Kernel width (mm) | 8.5 | 10 | 8 | 8 |
| Kernel thickness (mm) | 7 | 4 | 3 | 3 |
| Endosperm type | normal | normal | normal | normal |
| Endosperm color | yellow | yellow | yellow | yellow |

*These are typical values. Values may vary due to environment. Other values that are substantially equivalent within the scope of the invention.
"N/A": not available Thus, one aspect of the invention provides a novel maize hybrid variety designated ICH19849. Maize variety ICH19849 is a hybrid maize variety produced from a cross of two inbred maize lines, designated "female inbred variety 1" (RR728-18; ATCC Accession number PTA-5628) and "male inbred variety 1" (LH185; ATCC Accession number 75618). One embodiment includes a maize (*Zea mays*) plant designated ICH19849, wherein representative seed of the maize variety ICH19849 has been deposited under ATCC Accession number PTA-126949. Another embodiment includes an essentially homogeneous population of maize plants of the maize variety designated ICH19849, for example, an essentially homogeneous population of maize plants of the maize variety designated ICH19849, wherein representative seed of the maize variety ICH19849 has been deposited under ATCC Accession number PTA-126949. An embodiment includes a maize plant of the maize variety designated ICH19849, wherein representative seed of the maize variety ICH19849 has been deposited under ATCC Accession number PTA-126949, wherein the maize plant is grown from seed that has been deposited under ATCC Accession number PTA-126949. Yet another embodiment includes a maize plant that has or is characterized by all the morphological and physiological characteristics of the maize variety designated ICH19849.

In an embodiment, the maize plant of the maize variety designated ICH19849 further includes in its genome a transgene introduced by stable or transient transformation, for example, stable or transient transformation of either the maize plant of the maize variety designated ICH19849 or of one or both of its parent lines. In embodiments, a maize plant of the maize variety designated ICH19849 further includes in its genome a transgene encoding a protein (e.g., an insecticidal protein or an herbicide-resistance protein) or encoding an RNA molecule (e.g., a microRNA or a double-stranded RNA for RNAi-mediated suppression of a targeted genetic sequence) that provides a desirable trait such as improved resistance to a pest or pathogen, herbicide resistance, nutritional composition, and/or improved yield.

A related aspect of the invention is a seed that produces the maize plant of the maize variety designated ICH19849, wherein representative seed of the maize variety ICH19849 has been deposited under ATCC Accession number PTA-126949. One embodiment includes representative seed of the maize variety ICH19849 that has been deposited under ATCC Accession number PTA-126949. Another embodiment is a seed produced through maize breeding that produces the maize plant of the maize variety designated ICH19849, e.g., a maize plant that has or is characterized by all the morphological and physiological characteristics of maize variety ICH19849. Related aspects include a composition including a seed that produces the maize plant of the maize variety designated ICH19849 and a growth medium, such as soil or a synthetic or artificial medium.

A related aspect of the invention is a plant part of the maize plant of the maize variety designated ICH19849, wherein representative seed of the maize variety ICH19849 has been deposited under ATCC Accession number PTA-126949. In embodiments, the plant part includes or is a pollen grain, a silk, a tassel, an anther, an ovule, meristem, root, leaf, shoot, or shoot apex. A specific embodiment is a seed or seeds produced on the maize plant of the maize variety designated ICH19849. Other embodiments include any part or portion of the maize plant of the maize variety designated ICH19849, or combinations thereof. Related aspects further include a protoplast, cell, tissue culture, or callus from, or derived from (e.g., using tissue culture techniques) the maize plant of the maize variety designated ICH19849, as well as a maize plantlet or plant regenerated from such a protoplast, cell, tissue culture, or callus. Embodiments include a callus or tissue culture containing regenerable cells of a maize plant of the maize variety designated ICH19849, capable of regenerating plants capable of expressing all the physiological and morphological characteristics of the maize variety designated ICH19849, and of regenerating plants having substantially the same genotype as other plants of the maize variety designated ICH19849; in embodiments, such regenerable cells are obtained or derived from immature or mature embryos, meristem, immature or mature tassels or silk, microspores, pollen, anthers, leaves, stems, roots or root tips, silk, flowers, seeds, or other parts or tissue of a plant or seed of the maize variety designated ICH19849.

Related aspects of the invention include a seed of the maize variety designated ICH19849, wherein representative seed of the maize variety designated ICH19849 has been deposited under ATCC Accession number PTA-126949. An embodiment is an essentially homogeneous population of maize seeds of the maize variety designated ICH19849, wherein representative seed of the maize variety designated ICH19849 has been deposited under ATCC Accession number PTA-126949. Such an essentially homogeneous population of maize seeds of the maize variety designated ICH19849 can be provided in a container, such as a bag, or can include an essentially homogeneous population of maize seeds planted in a field. A related aspect of the invention includes a method of producing maize seed, including cultivating the maize plant of the maize variety designated ICH19849, wherein representative seed of the maize variety designated ICH19849 has been deposited under ATCC Accession number PTA-126949. A further related aspect of the invention is a method of producing a commodity maize product, the method including obtaining the maize plant of the maize variety designated ICH19849, or a part of the plant, and producing the commodity maize product therefrom. In various embodiments, the commodity maize products include products such as maize grain; maize starch, carbohydrates, sugars, and fermentation products thereof; maize seed oil; maize syrup; maize protein; and animal feed or fodder including silage.

Another related aspect of the invention is a maize plant having essentially all the physiological and morphological characteristics of a maize plant of the maize variety designated ICH19849 (wherein representative seed of the maize variety ICH19849 has been deposited under ATCC Accession number PTA-126949), and further characterized by having at least one additional trait selected from the group consisting of improved abiotic stress tolerance, improved biotic stress tolerance, modified nutritional content, modified metabolism, herbicide resistance, and modified fertility. In this context, "essentially all the morphological and physiological characteristics" refers to all the characteristics of a plant of the maize variety designated ICH19849 as provided in Table 1; it is understood that these characteristics can vary in maize plants that are grown under different conditions or in different environments, and therefore for the purpose of comparison of a maize plant's characteristics with those of the disclosed maize variety ICH19849, the maize plant is grown under the same conditions or same environment, and a small amount of variation (generally 5% or less) is acceptable. In embodiments, the additional trait is provided by a genetic locus that is a dominant or recessive allele, which includes, e.g., a naturally occurring maize gene that is introduced into the genome of a parent of maize variety ICH19849 by backcrossing, or is a natural or induced mutation, or is one or more transgenes introduced through genetic transformation techniques. Embodiments of improved abiotic stress tolerance include improved tolerance to water (drought or flooding), nutrient (nutrient deficiency or excess), temperature (heat or cold), or light (insufficient or excessive) stress. Embodiments of improved biotic stress tolerance include improved tolerance to crowding, shading, pests or pathogens (e.g., insect, arthropod, or nematode pests or fungal, bacterial, or viral pathogens). Embodiments of modified nutritional content include modified protein or amino acid content, modified fatty acid or lipid content, modified carbohydrate content (e.g., waxy starch), modified vitamin or pro-vitamin (e.g., vitamin A or pro-vitamin A or carotenoid) content, or modified lignin, allergen, antifeedant, or toxin (e.g., mycotoxin) content. Embodiments of modified metabolism include modifications to biochemical pathways involved in carbohydrate, protein, or fatty acid metabolism. Embodiments of herbicide resistance include resistance to herbicides commercially used in managing maize crops, e.g., glyphosate, ALS inhibitors, and other herbicides; see, e.g., the information below under the heading "Herbicide Resistance". Embodiments of modified fertility include male or female sterility, and fertility restoration. An embodiment is a maize plant that has essentially all the physiological and morphological characteristics of a maize plant of the maize variety designated ICH19849 and in addition is characterized by having a cytoplasmic or nuclear factor that is capable of conferring male sterility or otherwise preventing self-pollination, such as by self-incompatibility. In an embodiment, the trait is cytoplasmically inherited male sterility ("CMS"), a trait passed on to progeny through the female parent and characterized by pollen abortion when restorer genes are absent in the nucleus. In the presence of normal cytoplasm or restorer gene(s) in the nucleus, a CMS maize plant produces normal pollen. Thus, a CMS maize plant can be pollinated by a maintainer version of the same variety, which has a normal cytoplasm but lacks the restorer gene(s) in the nucleus, and continues to be male sterile in the next generation. Alternatively, male fertility of a CMS plant can be restored by a restorer version of the same variety that has the restorer gene(s) in the nucleus; the resulting progeny plants produce normal pollen.

In embodiments, the at least one additional trait is introduced using at least one process selected from the group consisting of transformation, genome editing, base editing, epigenetic modification, mutagenesis, and selection of either the maize plant of the maize variety designated ICH19849 or of its parents. Techniques for carrying out these processes are known to one of skill in the art and can be employed singly or in combination in order to effect introduction of the at least one additional trait into the maize plant that otherwise has essentially all the physiological and morphological characteristics of a maize plant of the maize variety designated ICH19849. Embodiments of transformation processes include transient transformation or stable transformation or a combination of both. Embodiments include a single transformation procedure (e.g., direct transformation of a plant, a cell or protoplast, a plant part or tissue or seed, or an embryo, germline cell, or pollen of the maize variety designated ICH19849), or multiple transformation procedures (e.g., transformation of a plant, a cell or protoplast, a plant part or tissue or seed, or an embryo, germline cell, or pollen of one or both parent lines of the maize variety designated ICH19849, and optionally also of the maize variety designated ICH19849). In non-limiting embodiments, for example, the at least one process includes use of at least one agent selected from a bacterium (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) that is capable of transforming a plant cell; a particle or nanoparticle (e.g., nano- or microparticles, nano- or microneedles, nano- or microfibers, and similar materials used to deliver a polynucleotide or polypeptide reagent in a transformation, genome editing, or base editing process); a recombinant DNA vector (e.g., a DNA polynucleotide or DNA plasmid or viral vector encoding at least one expression construct for expressing one or more polynucleotides or polypeptides); a nuclease (e.g., a TAL-effector nuclease, zinc finger nuclease, Cas nuclease, or an Argonaut) or a fusion protein or protein complex including one or more of such nucleases, whether active or inactive, covalently or non-covalently linked to another polypeptide domain that provides a desired functionality or polynucleotide(s) encoding the nuclease or fusion protein or protein complex, and optionally polynucleotides associated with the nuclease (such as guide RNAs associated with a Cas nuclease). Nucleases in combination with other proteins or polypeptide domains are described in more detail below under the heading "Nucleases and Their Combinations". In embodiments, the at least one additional trait is introduced using at least one selection step, or multiple selection steps, or recurrent selection steps in order to arrive at a maize plant having the desired additional traits in combination with essentially all the physiological and morphological characteristics of a maize plant of the maize variety designated ICH19849. A selection step can include exposing a population of maize plants or seedlings (or cells or callus under tissue culture conditions) to conditions permitting expression of the additional trait. For example, selection for herbicide resistance can include exposing a population of maize plants to an amount of herbicide that inhibits growth or is toxic, allowing identification and selection of those resistant maize plants that survive treatment and are then selected for the next breeding cycle. In certain embodiments, a proxy measurement indicative of a desired phenotype or trait is used for selection. For example, selecting for a trait characterized by increased expression of an enzyme may be determined by detecting lower levels of the enzyme's substrate in the tested plants.

In related embodiments, the at least one additional trait is associated with a transgene that is introduced into by backcrossing or genetic transformation of a maize plant designated ICH19849. Embodiments of transgenes of interest include transgenes encoding polypeptides or polynucleotides (e.g., miRNAs) that provide a phenotype of interest that is in addition to essentially all the physiological and morphological characteristics of a maize plant of the maize variety designated ICH19849. Non-limiting examples of such phenotypes of interest include herbicide resistance; improved tolerance of abiotic stress (e.g., tolerance of temperature extremes, drought, or salt) or biotic stress (e.g., resistance to bacterial or fungal pathogens); improved utilization of nutrients or water; synthesis of new or modified amounts of lipids, carbohydrates, proteins or other chemicals, including medicinal compounds; improved flavor or appearance; improved photosynthesis; improved storage characteristics (e.g., resistance to bruising, browning, or softening); increased yield; certain alterations in morphology (e.g., root structure) that do not otherwise change the morphological characteristics of a maize plant of the maize variety designated ICH19849; and changes in flowering time. Embodiments of modified fertility include male or female sterility, and fertility restoration. An embodiment is a maize plant that has essentially all the physiological and morphological characteristics of a maize plant of the maize variety designated ICH19849 and in addition is characterized by expressing a transgene that is capable of conferring male sterility, optionally under specific growing conditions, for example a transgene that expresses a protein that confers herbicide resistance, and a miRNA or small RNA that prevents expression of the herbicide resistance in male reproductive tissue, resulting in male sterility induced by application of the herbicide to the maize plant; see, e.g., the methods and genetic constructs for providing inducible male sterility in plants disclosed in U.S. Pat. Nos. 8,334,430 and 9,139,838, the disclosures of which are incorporated by reference in their entirety herein.

An aspect of the invention provides a method of producing a progeny maize seed derived from maize variety ICH19849, including harvesting seed of a progeny maize plant obtained by crossing a maize plant of the maize variety designated ICH19849, wherein representative seed of the maize variety ICH19849 has been deposited under ATCC Accession number PTA-126949 with itself or with a second maize plant, thereby producing progeny maize seed. A related aspect of the invention thus includes the progeny maize seed produced by this method.

A further aspect of the invention provides a method of producing a ICH19849-derived maize plant, wherein the method including the step of applying to a maize plant of the maize variety designated ICH19849, wherein representative seed of the maize variety ICH19849 has been deposited under ATCC Accession number PTA-126949, at least one plant breeding technique selected from the group consisting of: selfing, backcrossing, outcrossing, marker-assisted selection or marker-assisted breeding, pedigree breeding, haploid production, doubled haploid production, and transformation, thereby producing a ICH19849-derived maize plant; a related aspect of the invention is the ICH19849-derived maize plant produced by the method. For example, a maize plant of the maize variety designated ICH19849 is crossed with a second maize plant of a different, distinct variety to provide a ICH19849-derived progeny plant that has, as either its male or its female parent, the maize variety ICH19849; such a crossing procedure results in the production of seed, which can be grown into the ICH19849-derived progeny plant. In embodiments, the method includes (1) the step of applying to a maize plant of the maize variety designated ICH19849, wherein representative seed of the maize variety ICH19849 has been deposited under ATCC Accession number PTA-126949, at least one plant breeding technique selected from the group consisting of: selfing, backcrossing, outcrossing, marker-assisted selection or marker-assisted breeding, pedigree breeding, haploid production, doubled haploid production, and transformation, thereby producing a ICH19849-derived maize plant; and further includes (2) the step of crossing the ICH19849-derived maize plant with itself or with a second maize plant to produce a seed of a progeny plant of a subsequent generation. A related aspect of the invention is the seed produced by this method, or the progeny plant of a subsequent generation that is grown from the seed; another related aspect of the invention provides a method of producing a nucleic acid preparation, including extracting nucleic acids from the seed of a progeny plant of a subsequent generation, or from a plant grown from the seed, or from a cell, cell culture, tissue culture, or callus obtained from the seed. In yet further embodiments, the method includes (1) the step of applying to a maize plant of the maize variety designated ICH19849, wherein representative seed of the maize variety ICH19849 has been deposited under ATCC Accession number PTA-126949, at least one plant breeding technique selected from the group consisting of: selfing, backcrossing, outcrossing, marker-assisted selection or marker-assisted breeding, pedigree breeding, haploid production, doubled haploid production, and transformation, thereby producing a ICH19849-derived maize plant; and further includes the steps of: (2) crossing the ICH19849-derived maize plant with itself or with a second maize plant to produce a next-generation seed; (3) growing from the next-generation seed a next-generation progeny plant; and (4) repeating with the resulting next-generation progeny plant additional crossing steps with itself or with a different maize plant for at least an additional (1-10) generation to produce a progeny maize plant further derived from maize variety ICH19849.

Yet another aspect of the invention provides a method of producing a nucleic acid preparation, including extracting nucleic acids from a maize plant of the maize variety designated ICH19849, wherein representative seed of the maize variety ICH19849 has been deposited under ATCC Accession number PTA-126949, or from a cell or part of the maize plant, or from its seed. The extracted nucleic acids are useful especially for genetic analysis of the maize plant or its seed. Thus, a related aspect of the invention provides a method of producing a genetic marker profile including genotyping nucleic acids extracted from the maize plant designated ICH19849 or from the representative seed deposited under ATCC Accession number PTA-126949, thereby producing a genetic marker profile. Another related aspect of the invention provides a method of maize breeding including identifying at least one genetic polymorphism (e.g., a single nucleotide polymorphism (SNP), a specific allele, or one or more mutations) in nucleic acids extracted from the maize plant designated ICH19849 or from the representative seed deposited under ATCC Accession number PTA-126949, and selecting a maize plant identified as having the at least one genetic polymorphism, wherein the selected maize plant is used in a maize breeding method to produce a progeny maize plant; also encompassed by the invention is the progeny maize plant produced by this method of maize breeding.

A further aspect of the invention provides a method for producing an inbred maize plant including crossing a maize plant of the maize variety designated ICH19849, wherein representative seed of the maize variety ICH19849 has been deposited under ATCC Accession number PTA-126949, with a haploid inducer variety to produce haploid seed, and doubling the haploid seed, thereby producing an inbred maize plant.

Embodiments of the invention provided herein include but are not limited to the following numbered embodiments.

1. A maize plant of the maize variety designated ICH19849, wherein representative seed of the maize variety ICH19849 has been deposited under ATCC Accession number PTA-126949.

2. The maize plant of embodiment 1, which is grown from seed that has been deposited under ATCC Accession number PTA-126949.

3. A maize plant having all the physiological and morphological characteristics of the plant of embodiment 1.

4. The maize plant of embodiment 1, further comprising in its genome a transgene introduced by stable or transient transformation.

5. A seed that produces the maize plant of embodiment 1.

6. A composition comprising the seed of embodiment 5 and a growth medium.

7. The composition of embodiment 6, wherein the growth medium is soil or a synthetic medium.

8. A plant part of the maize plant of embodiment 1, wherein the plant part is a pollen grain, a silk, a tassel, an anther, an ovule, meristem, root, leaf, shoot, or shoot apex.

9. A protoplast, cell, tissue culture, or callus from the maize plant of embodiment 1.

10. A maize plantlet or plant regenerated from the protoplast, cell, tissue culture, or callus of embodiment 9.

11. A maize seed produced on the maize plant of embodiment 1.

12. A seed of maize variety ICH19849, wherein representative seed of the maize variety ICH19849 has been deposited under ATCC Accession number PTA-126949.

13. A method of producing maize seed, comprising cultivating the maize plant of embodiment 1 and harvesting seed from the plant.

14. A method of producing a commodity maize product, the method comprising obtaining the maize plant of embodiment 1 or a part of the plant, and producing the commodity maize product therefrom.

15. The method of embodiment 14, wherein the commodity maize product is at least one selected from the group of commodity maize products consisting of: maize grain; maize starch, carbohydrates, sugars, and fermentation products thereof; maize seed oil; maize syrup; maize protein; and animal feed or fodder.

16. A maize plant having essentially all the physiological and morphological characteristics of the maize plant of embodiment 1 and further characterized by having at least one additional trait selected from the group consisting of improved abiotic stress tolerance, improved biotic stress tolerance, modified nutritional content, modified metabolism, herbicide resistance, and modified fertility.

17. The maize plant of embodiment 16, wherein the at least one additional trait is introduced using at least one process selected from the group consisting of transformation, genome editing, base editing, epigenetic modification, mutagenesis, and selection.

18. The maize plant of embodiment 17, wherein the at least one process comprises use of at least one agent selected from: a bacterium capable of transforming a plant cell; a particle or nanoparticle; a recombinant DNA vector; and a nuclease, or a fusion protein or protein complex including a nuclease, and optionally polynucleotides associated with the nuclease.

19. The maize plant of embodiment 16, wherein the at least one additional trait is associated with a transgene that is introduced into by backcrossing or genetic transformation of a maize plant designated ICH19849.

20. A method of producing a progeny maize seed derived from maize variety ICH19849, comprising harvesting seed of a progeny maize plant obtained by crossing the maize plant of embodiment 1 with itself or with a second maize plant, thereby producing progeny maize seed.

21. The progeny maize seed produced by the method of 20.

22. A method of producing a ICH19849-derived maize plant, the method comprising applying to the maize plant of embodiment 1 at least one plant breeding technique selected from the group consisting of: selfing, backcrossing, outcrossing, marker-assisted selection or breeding, pedigree breeding, haploid production, doubled haploid production, and transformation, thereby producing a ICH19849-derived maize plant.

23. The ICH19849-derived maize plant produced by the method of embodiment 22.

24. The method of embodiment 22, further comprising the step of: crossing the ICH19849-derived maize plant with itself or with a second maize plant to produce a seed of a progeny plant of a subsequent generation.

25. The seed produced by the method of 24, or the progeny plant of a subsequent generation grown from the seed.

26. A method of producing a nucleic acid preparation, comprising extracting nucleic acids from the seed of embodiment 25, or from a plant grown from the seed, or from a cell, cell culture, tissue culture, or callus obtained from the seed.

27. The method of embodiment 22, further comprising the steps of: (a) crossing the ICH19849-derived maize plant with itself or with a second maize plant to produce a next-generation seed; (b) growing from the next-generation seed a next-generation progeny plant; and (c) repeating with the resulting next-generation progeny plant additional crossing steps with itself or with a different maize plant for at least an additional generation to produce a progeny maize plant further derived from maize variety ICH19849.

28. A method of producing a nucleic acid preparation, comprising extracting nucleic acids from the maize plant of embodiment 1, or from a cell or part of the maize plant, or from its representative seed deposited under ATCC Accession number PTA-126949.

29. A method of producing a genetic marker profile comprising genotyping nucleic acids extracted from the maize plant designated ICH19849 or from the representative seed deposited under ATCC Accession number PTA-126949, thereby producing a genetic marker profile.

30. A method of maize breeding comprising identifying at least one genetic polymorphism in nucleic acids extracted from the maize plant designated ICH19849 or from the representative seed deposited under ATCC Accession number PTA-126949, and selecting a maize plant identified as having the at least one genetic polymorphism, wherein the selected maize plant is used in a maize breeding method.

31. A maize plant produced by the method of embodiment 30.

32. A method for producing an inbred maize plant comprising crossing the maize plant of embodiment 1 with a haploid inducer variety to produce haploid seed, and doubling the haploid seed, thereby producing an inbred maize plant.

33. A maize plant having essentially all the physiological and morphological characteristics of the maize plant of embodiment 1 and further characterized by glyphosate herbicide resistance.

Deposit Information 1001721A deposit of at least 625 seeds of the hybrid maize line ICH19849 is made on Jan. 15, 2021 with the American Type Culture Collection (ATCC), located at 10801 University Boulevard, Manassas, VA 20110-2209, United States of America, and assigned ATCC Accession number PTA-126949. The deposits are made pursuant to the terms of the Budapest Treaty, and are intended to meet the requirements of 37 CFR § 1.801-1.809. Access to the seed deposits will be available upon request during the pendency of the application to the Commissioner of Patents and Trademarks and persons determined by the Commissioner to be entitled thereto. All restrictions upon availability to the public will be irrevocably removed upon granting of the patent. The deposit will be maintained in the ATCC Depository, which is a public depository, for a period of 30 years, or 5 years after the most recent request, or for the enforceable life of the patent, whichever is longer. The viability of the deposit will be tested and will be replaced if it becomes nonviable during that period. Upon allowance of any claims in the application, Applicant will maintain and will make this deposit available to the public, pursuant to the Budapest Treaty. Applicant does not waive any infringement of Applicant's rights granted under this patent or under the Plant Variety Protection Act (7 U.S.C. 2321 et seq.).

Related Disclosure

Nucleases and Their Combinations

Various aspects of the invention are related to maize plants of the maize hybrid variety ICH19849 as described herein, that have one or more additional traits in addition to essentially all the characteristics of the variety (e.g., as described, in Table 1). In embodiments, the one or more additional trait is introduced into a maize plant of the maize hybrid variety ICH19849 (or, alternatively, into one or both parents of the variety) with a procedure using one or more nucleases. For example, the genome of a maize plant of the maize hybrid variety ICH19849 can subjected to a genome editing procedure using a site-specific nuclease that modifies the genome at a predetermined location. Site-specific nucleases useful for this purpose include Cas nucleases, zinc finger nucleases, TALENs, and Argonautes. In related embodiments, a Cas nuclease, zinc finger nuclease, TALEN, or Argonaute is used in conjunction with other functional domains, which can be combined with the nuclease through a protein fusion or through other covalent or non-covalent linkages or complexes. The nuclease itself can be normally functional, or can be a deactivated variant; for example, the nuclease activity of these nucleic acid targeting systems can be altered so that the nuclease binds to but does not cleave the DNA at the predetermined location. Examples of functional domains that can be used in combination with an active or deactivated nuclease include transposase domains, integrase domains, recombinase domains, resolvase domains, invertase domains, protease domains, DNA methyltransferase domains, DNA hydroxylmethylase domains, DNA demethylase domains, histone acetylase domains, histone deacetylase domains, nuclease domains, repressor domains, activator domains, nuclear-localization signal domains, transcription-regulatory protein (or transcription complex recruiting) domains, cellular uptake activity associated domains, nucleic acid binding domains, antibody presentation domains, histone modifying enzymes, recruiter of histone modifying enzymes; inhibitor of histone modifying enzymes, histone methyltransferases, histone demethylases, histone kinases, histone phosphatases, histone ribosylases, histone deribosylases, histone ubiquitinases, histone deubiquitinases, histone biotinases and histone tail proteases. Non-limiting examples of functional domains include a transcriptional activation domain, a transcription repression domain, and an SHH1, SUVH2, or SUVH9 polypeptide capable of reducing expression of a target nucleotide sequence via epigenetic modification; see, e.g., U.S. Patent Application Publication 2016/0017348, incorporated herein by reference in its entirety. Genomic DNA may also be modified via base editing using a fusion between a catalytically inactive Cas9 (dCas9) is fused to a cytidine deaminase which convert cytosine (C) to uridine (U), thereby effecting a C to T substitution; see Komor et al. (2016) *Nature*, 533:420-424.

Maize Breeding

Embodiments of the invention include maize breeding procedures, such as crossing two maize parent plants, which are often of distinct genetic background or "lines". Maize crossing typically involves planting, conveniently in pollinating proximity, seeds of a first and second parent maize plant, which can be of different lines; the resulting seedlings are grown into plants of reproductive maturity, and generally are prevented from self-pollinating (e.g., by physical emasculation of the plant meant to serve as the female parent or by use of a chemical gametocide). Plants not within pollinating proximity can be pollinated by transferring pollen from one plant to the other. (Self-incompatibility systems may also be used in some hybrid crops for the same purpose. Self-incompatible plants still shed viable pollen and can pollinate plants of other varieties but are incapable of pollinating themselves or other plants of the same variety.) Finally, the resulting seed from at least one of the parent maize plants is harvested, thus providing progeny seed that can be grown to produce a progeny maize plant.

Tissue Culture

As used herein, the term "tissue culture" indicates a composition comprising isolated cells of the same or a different type or a collection of such cells organized into parts of a plant. Exemplary types of tissue cultures are protoplasts, calli, and plant cells that are intact in plants or parts of plants, such as embryos, pollen, flowers, kernels, ears, cobs, leaves, husks, stalks, roots, root tips, anthers, silk, and the like. In one embodiment, the tissue culture comprises embryos, protoplasts, meristematic cells, pollen, leaves or anthers derived from immature tissues of these plant parts.

Means for preparing and maintaining plant tissue cultures are well known in the art (U.S. Pat. Nos. 5,538,880 and 5,550,318, each incorporated herein by reference in their entirety). Examples of processes of tissue culturing and regeneration of maize are described in, for example, European Patent Application Publication No. EP0160390, Green and Rhodes (In: Maize for Biological Research, 367, 1982) and Duncan et al. (Planta, 165:322, 1985), Songstad et al. (Plant Cell Reports, 7:262, 1988), Rao et al. (Maize Genetics Cooperation Newsletter, 60, 1986), Conger et al. (Plant Cell Reports, 6:345, 1987), PCT Application WO 95/06128, Armstrong and Green (Planta, 164:207, 1985); Gordon-Kamm et al. (The Plant Cell, 2:603, 1990), and U.S. Pat. No. 5,736,369. One type of tissue culture is tassel/anther culture to produce regenerated plants. Exemplary methods of microspore culture are disclosed in, for example, U.S. Pat. Nos. 5,322,789 and 5,445,961, the disclosures of which are specifically incorporated herein by reference.

Haploid and Doubled-Haploid Plants

Uniform lines of new varieties may also be developed by way of doubled-haploids. This technique allows the creation of true breeding lines without the need for multiple generations of selfing and selection. In this manner true breeding lines can be produced in as little as one generation. Haploid induction systems have been developed for various plants to produce haploid tissues, plants and seeds. The haploid induction system can produce haploid plants from any genotype by crossing with an inducer line. Inducer lines and methods for obtaining haploid plants are known in the art.

Haploid embryos may be produced, for example, from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. Such techniques can be used with maize plants of the maize hybrid variety ICH19849 as described herein, or with derived or progeny plants thereof, to achieve a homozygous line.

Backcrossing

In the plant breeding technique called backcrossing, essentially all the morphological and physiological characteristics of an original variety are recovered or retained in the resultant plant obtained by the backcrossing process, in addition to a genetic locus transferred into the resultant plant via the backcrossing technique. By essentially all the morphological and physiological characteristics, it is meant that all the characteristics of the original plant are recovered or retained in the resultant plant obtained by the backcrossing process, other than an occasional variant trait that might arise during backcrossing or direct introduction of a transgene.

Backcrossing methods can be used with maize plants maize plants of the maize hybrid variety ICH19849 as described herein to improve a characteristic or introduce a trait of interest. "Backcrossing" refers to the repeated crossing of a hybrid progeny back to one of the hybrid's two parental lines, which is termed the recurrent parent as it is used in several breeding rounds in the backcrossing process. The parental maize plant which contributes the locus or loci for the trait is termed the nonrecurrent or donor parent as it is used only once in the backcrossing process. The transferred locus can be, e.g., a dominant or a recessive allele, which can include a naturally occurring genetic sequence or can include a transgene that confers the trait of interest. The parental maize plant to which the locus or loci from the nonrecurrent parent are transferred is known as the recurrent parent as it is used for several rounds in the backcrossing process. In a typical backcrossing process, the original parent hybrid of interest (recurrent parent) is crossed to a second variety (nonrecurrent parent) that carries the genetic locus of interest to be transferred. The resulting progeny from this cross are then crossed again to the recurrent parent and the process is repeated until a maize plant is obtained wherein essentially all the morphological and physiological characteristics of the recurrent parent are recovered in the converted plant, in addition to the transferred locus from the nonrecurrent parent. The backcrossing process may be accelerated using genetic markers, such as simple sequence repeats (SSRs), restriction fragment length polymorphisms (RFLPs), amplified fragment length polymorphisms (AFLPs), single nucleotide polymorphisms (SNPs), and isozyme markers to identify plants with the greatest genetic complement from the recurrent parent. In certain cases, direct selection can be used to identify plants in a given generation that have the transferred locus; for example, plants that contain in their genome a transgene that confers herbicide resistance can be identified and selected by application of the herbicide prior to the next backcrossing step, which eliminates plants lacking the transgene.

A plant of any generation in a breeding program can be characterized by genetic analysis, thus describing its "genetic complement", that is to say, the totality of genetic sequences, the expression of which defines the phenotype of the plant, or of a cell or tissue of the plant. An aspect of this invention thus provides maize plant cells that have a genetic complement in accordance with that of a maize plant of the maize hybrid variety ICH19849 as described herein, and plants or seeds containing such cells. A plant's genetic complement may be assessed by obtaining a genetic marker profile from nucleic acids extracted from the plant, and by the expression of phenotypic traits that are characteristic of the expression of the genetic complement, e.g., genetic marker typing profiles. Genetic marker types include Simple Sequence Repeats (SSRs), Simple Sequence Length Polymorphisms (SSLPs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs), and Single Nucleotide Polymorphisms (SNPs). Another aspect of the invention provides hybrid genetic complements, as represented by maize plant cells, tissues, plants, and seeds, formed by the combination of a haploid genetic complement of a maize plant of the maize hybrid variety ICH19849 as described herein, with a haploid genetic complement of the same or a different variety. Another aspect of the invention provides a maize plant regenerated from a tissue culture that includes a genetic complement of a maize plant of the maize hybrid variety ICH19849 as described herein.

Growth Media

Embodiments of the invention include compositions including a seed of a maize variety disclosed herein and a growth medium. Suitable growth media are known to those of skill in the art of growing and breeding maize, and include natural or amended soils and synthetic or artificial growth media, for example, as described in U.S. Pat. Nos. 3,932,166, 4,707,176, and 4,241,537, the disclosures of which are incorporated by reference in their entirety herein.

Traits and Their Introduction

Useful traits can be introduced by genetic transformation techniques, for example by transformation to stably integrate into a plant's genome a transgene that confers the trait. In some embodiments, a trait is associated with a specific allele which can be fixed into a plant variety by breeding techniques such as backcrossing (see the section under the heading "Backcrossing"). In other embodiments, the plant's genome can be specifically modified, e.g., by genome editing, base editing, or epigenetic modification, in order to introduce a desirable trait that is associated with the modification.

Methods for the genetic transformation of maize are known to those of skill in the art. For example, methods which have been described for the genetic transformation of maize include electroporation (U.S. Pat. No. 5,384,253), electrotransformation (U.S. Pat. No. 5,371,003), microprojectile bombardment (U.S. Pat. Nos. 5,550,318, 5,736,369 and 5,538,880; and PCT Publication WO 95/06128), *Agrobacterium*-mediated transformation (U.S. Pat. No. 5,591, 616 and European Patent Application Publication No. EP0672752), direct DNA uptake transformation of protoplasts, and silicon carbide fiber-mediated transformation (U.S. Pat. Nos. 5,302,532 and 5,464,765).

Certain embodiments involve methods for specifically modifying a plant's genome in order to modify a characteristic in the plant or to introduce a trait. Modifying the genome can be carried out at a predetermined locus, e.g., by genome editing, base editing, or epigenetic modification. Examples of such genomic modifications include deletion of at least one nucleotide, insertion of at least one nucleotide, and replacements of at least one nucleotide, as well as combinations of these. The modification is typically sequence-specific, that is to say, occurring at a pre-selected location in the genome, and can be in coding sequence or in non-coding sequence (e.g., in promoters and other regulatory sequences, or in intronic sequences) or in both coding and non-coding sequence. The techniques for such modifications are well known in the art and include, e.g., use of sequence-specific nucleases such as those used in CRISPR-Cas systems, zinc-finger nucleases (ZFNs), and transcription activator-like effector nucleases (TALENs). Suitable methods of genomic modification of plants including maize are disclosed in detail in U.S. Patent Application Publication 2019/0352655, which is incorporated by reference in its entirety herein.

Genetic Sequences Associated with Traits

Male Sterility: Examples of genes conferring male sterility include those disclosed in U.S. Pat. Nos. 3,861,709, 3,710,511, 4,654,465, 5,625,132, and 4,727,219, each of the disclosures of which are specifically incorporated herein by reference in their entirety. Male sterility genes can increase the efficiency with which hybrids are made, in that they eliminate the need to physically emasculate the maize plant used as a female parent in a given cross.

When one desires to employ male-sterility systems with a maize plant, it may be beneficial to also utilize one or more male-fertility restorer genes. For example, when cytoplasmic male sterility (CMS) is used, hybrid seed production requires three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent. The presence of a male-fertility restorer gene results in the production of fully fertile Fi hybrid progeny. If no restorer gene is present in the male parent, male-sterile hybrids are obtained. Such hybrids are useful when the vegetative tissue of the maize plant is utilized, e.g., for silage, but in most cases, the seeds will be deemed the most valuable portion of the crop, so fertility of the hybrids in these crops must be restored. One aspect of this disclosure thus provides a maize plant of the maize hybrid variety ICH19849 as described herein, comprising a genetic locus capable of restoring male fertility in an otherwise male-sterile plant. Examples of male-sterility genes and corresponding restorers which could be employed with a maize plant of the maize hybrid variety ICH19849 are known in the art; see, e.g., U.S. Pat. Nos. 5,530,191; 5,689,041; 5,741,684; and 5,684,242, the disclosures of which are each specifically incorporated herein by reference in their entirety.

Herbicide Resistance: Numerous herbicide resistance genes are known and may be employed with a maize plant disclosed and claimed herein. Embodiments include a gene conferring resistance to an acetolactate synthase (ALS)-inhibiting herbicide, such as the sulfonylurea herbicide nicosulfuron, that prevents the formation of branched chain amino acids and inhibits meristem growth. Resistance genes for glyphosate (resistance conferred by mutant 5-enolpyruvylshikimate-3-phosphate synthase (EPSPS) and aroA genes, respectively) and other phosphono compounds such as glufosinate (phosphinothricin acetyltransferase (PAT) and *Streptomyces hygroscopicus* phosphinothricin acetyltransferase (bar) genes) may also be used. See, for example, U.S. Pat. Nos. 4,940,835, 6,040,497, and 7,632, 985. A DNA molecule encoding a mutant aroA gene can be obtained under ATCC Accession No. 39256, and the nucleotide sequence of the mutant gene is disclosed in U.S. Pat. No. 4,769,061. In addition to glyphosate tolerant genes that may be used to make a plant glyphosate tolerant, glyphosate tolerant events may be crossed with the male or female inbred to create a glyphosate tolerant inbred, which results in ICH19849 glyphosate tolerant, see U.S. Pat. No. 6,040, 497 and ATTC Accession Number 209032, U.S. Pat. Nos. 6,762,344, and 7,314,970, all of which are incorporated herein by reference. A hygromycin B phosphotransferase gene that confers resistance to glyphosate is described in Penaloza-Vazquez et al., Plant Cell Reports, 14:482, 1995. European Patent Application Publication No. EP0333033 to Kumada et al., and U.S. Pat. No. 4,975,374 to Goodman et al., disclose nucleotide sequences of glutamine synthetase genes that confer resistance to herbicides such as L-phosphinothricin. The nucleotide sequence of a phosphinothricin acetyltransferase gene is provided in European Patent Application Publication No. EP0242246. DeGreef et al. (Biotechnology, 7:61, 1989) describe the production of transgenic plants that express chimeric bar genes coding for phosphinothricin acetyl transferase activity. Exemplary genes conferring resistance to a phenoxy class herbicide haloxyfop and a cyclohexanedione class herbicide sethoxydim are the Acct-S1, Acct-S2 and Acct-S3 genes; see Marshall et al., (1992) Theor. Appl. Genet., 83:435. As a non-limiting example, a gene may confer resistance to other exemplary phenoxy class herbicides that include, but are not limited to, quizalofop-p-ethyl and 2,4-dichlorophenoxyacetic acid (2,4-D). Genes are also known that confer resistance to herbicides that inhibit photosynthesis such as, for example, triazine herbicides (psbA and gs+genes) and benzonitrile herbicides (nitrilase gene). As a non-limiting example, a gene may confer resistance to the exemplary benzonitrile herbicide bromoxynil. Przibila et al. (Plant Cell, 3:169, 1991) describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al. (Biochem. J., 285:173, 1992). 4-hydroxyphenylpyruvate dioxygenase (HPPD) is a target of the HPPD-inhibiting herbicides, which deplete plant plastoquinone and vitamin E pools. Rippert et al. (Plant Physiol., 134:92, 2004) describes an HPPD-inhibitor resistant tobacco plant that was transformed with a yeast-derived prephenate dehydrogenase (PDH) gene. Protoporphyrinogen oxidase (PPO) is the target of the PPO-inhibitor class of herbicides; a PPO-inhibitor resistant PPO gene was recently identified in *Amaranthus tuberculatus* (Patzoldt et al., PNAS, 103(33):12329, 2006). The herbicide methyl viologen inhibits $CO_2$ assimilation. Foyer et al. (Plant Physiol., 109:1047, 1995) describe a plant overexpressing glutathione reductase (GR) that is resistant to methyl viologen treatment. Siminszky (Phytochemistry Reviews, 5:445, 2006) describes plant cytochrome P450-mediated detoxification of multiple, chemically unrelated classes of herbicides. Modified bacterial genes have been successfully demonstrated to confer resistance to atrazine, a herbicide that binds to the plastoquinone-binding membrane protein $Q_B$ in photosystem II to inhibit electron transport. See, for example, studies by Cheung et al. (PNAS, 85:391, 1988), describing tobacco plants expressing the chloroplast psbA gene from an atrazine-resistant biotype of *Amaranthus hybridus* fused to the regulatory sequences of a nuclear gene, and Wang et al. (Plant Biotech. J., 3:475, 2005), describing transgenic alfalfa, *Arabidopsis*, and tobacco plants expressing the atzA gene from *Pseudomonas* sp. that were able to detoxify atrazine. Bayley et al. (Theor. Appl. Genet., 83:645, 1992) describe the creation of 2,4-D-resistant transgenic tobacco and cotton plants using the 2,4-D monooxygenase gene tfdA from *Alcaligenes eutrophus* plasmid pJP5. U.S. Patent Application Publication No. 20030135879 describes the isolation of a gene for dicamba monooxygenase (DMO) from *Pseudomonas maltophilia* that is involved in the conversion of dicamba to a non-toxic 3,6-dichlorosalicylic acid and thus may be used for producing plants tolerant to this herbicide. Other examples of herbicide resistance have been described, for instance, in U.S. Pat. Nos. 6,803,501; 6,448,476; 6,248,876; 6,225,114; 6,107,549; 5,866,775; 5,804,425; 5,633,435; 5,463,175.

Waxy Starch: The waxy characteristic is an example of a recessive trait. In this example, the progeny resulting from the first backcross generation ($BC_1$) must be grown and selfed. A test is then run on the selfed seed from the $BC_1$ plant to determine which $BC_1$ plants carried the recessive gene for the waxy trait. In other recessive traits additional progeny testing, for example growing additional generations such as the $BC_1S_1$, may be required to determine which plants carry the recessive gene.

Disease Resistance: Plant defenses are often activated by specific interaction between the product of a disease resistance gene (R) in the plant and the product of a corresponding avirulence (Avr) gene in the pathogen. A plant line can be transformed with a cloned resistance gene to engineer plants that are resistant to specific pathogen strains. See, for example, Jones et al., Science, 266:789, 1994, which describes the cloning of the tomato Cf-9 gene for resistance to *Cladosporium flavum*; Martin et al., Science, 262:1432, 1993, which describes the tomato Pto gene for resistance to *Pseudomonas syringae* pv.; and Mindrinos et al., Cell, 78:1089, 1994, which describes the Arabidopsis RPS2 gene for resistance to *Pseudomonas syringae*.

A viral-invasive protein or a complex toxin derived therefrom may also be used for viral disease resistance. For example, the accumulation of viral coat proteins in transformed plant cells imparts resistance to viral infection and/or disease development effected by the virus from which the coat protein gene is derived, as well as by related viruses. See Beachy et al., (Annu. Rev. Phytopathol., 28:451, 1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. A virus-specific antibody may also be used. See, for example, Tavladoraki et al., (Nature, 366:469, 1993), who show that transgenic plants expressing recombinant antibody genes are protected from virus attack. Additional means of inducing whole-plant resistance to a pathogen include modulation of the systemic acquired resistance (SAR) or pathogenesis related (PR) genes, for example genes homologous to the *Arabidopsis thaliana* NIM1/NPR1/SAI1, and/or by increasing salicylic acid production (Ryals et al., Plant Cell, 8:1809, 1996).

Logemann et al., (Biotechnology, 10:305, 1992), for example, disclose transgenic plants expressing a barley ribosome-inactivating gene have an increased resistance to fungal disease. Plant defensins may be used to provide resistance to fungal pathogens (Thomma et al., Planta, 216:193, 2002). Other examples of fungal disease resistance are provided in U.S. Pat. Nos. 6,653,280; 6,573,361; 6,506,962; 6,316,407; 6,215,048; 5,516,671; 5,773,696; 6,121,436; 6,316,407; and 6,506,962.

Insect Resistance: One example of an insect resistance gene includes a *Bacillus thuringiensis* (Bt) protein, a derivative thereof or a synthetic polypeptide modeled thereon. See, for example, Geiser et al., (Gene, 48:109, 1986), who disclose the cloning and nucleotide sequence of a Bt .delta.-endotoxin gene. Moreover, DNA molecules encoding .delta.-endotoxin genes can be purchased from the American Type Culture Collection, Manassas, Va., for example, under ATCC Accession Nos. 40098, 67136, 31995 and 31998. Another example is a lectin. See, for example, Van Damme et al., (Plant Molec. Biol., 24:825, 1994), who disclose the nucleotide sequences of several *Clivia miniata* mannose-binding lectin genes. A vitamin-binding protein may also be used, such as avidin. PCT application US93/06487 teaches the use of avidin and avidin homologues as larvicides against insect pests.

Yet another insect resistance gene is an enzyme inhibitor, for example, a protease or proteinase inhibitor or an amylase inhibitor. See, for example, Abe et al., (J. Biol. Chem., 262:16793, 1987), which describes the nucleotide sequence of rice cysteine proteinase inhibitor, Huub et al., (Plant Molec. Biol., 21:985, 1993), which describes the nucleotide sequence of cDNA encoding tobacco proteinase inhibitor I, and Sumitani et al., (Biosci. Biotech. Biochem., 57:1243, 1993), which describes the nucleotide sequence of *Streptomyces nitrosporeus* .alpha.-amylase inhibitor).

An insect-specific hormone or pheromone may also be used. See, for example, Hammock et al., (Nature, 344:458, 1990), which describes baculovirus expression of cloned juvenile hormone esterase, an inactivator of juvenile hormone, Gade and Goldsworthy (eds.) (Physiological Systems in Insects, Elsevier Academic Press, Burlington, Mass., 2007), which describes allostatins and their potential use in pest control; and Palli et al., (Vitam. Horm., 73:59, 2005), which describes the use of ecdysteroid and ecdysteroid receptor in agriculture. Additionally, the diuretic hormone receptor (DHR) was identified in Price et al., (Insect Mol. Biol., 13:469, 2004) as a candidate target of insecticides.

Still other examples include an insect-specific antibody or an immunotoxin derived therefrom and a developmental-arrestive protein. See Taylor et al., (Seventh Intl Symposium on Molecular Plant-Microbe Interactions, Edinburgh, Scotland, Abstract W97, 1994), who described enzymatic inactivation in transgenic tobacco via production of single-chain antibody fragments. Nematode resistance has been described, for example, in U.S. Pat. No. 6,228,992 and bacterial disease resistance in U.S. Pat. No. 5,516,671.

Modified Fatty Acid, Phytate, and Carbohydrate Metabolism: Genes may be used conferring modified fatty acid metabolism. For example, stearyl-ACP desaturase genes may be used. See Knutzon et al., (Proc. Natl. Acad. Sci. USA, 89:2624, 1992). Various fatty acid desaturases have also been described, such as a *Saccharomyces cerevisiae* OLE1 gene encoding .DELTA.9 fatty acid desaturase, an enzyme which forms the monounsaturated palmitoleic (16:1) and oleic (18:1) fatty acids from palmitoyl (16:0) or stearoyl (18:0) CoA (McDonough et al., J. Biol. Chem., 267(9):5931-5936, 1992); a gene encoding a stearoyl-acyl carrier protein delta-9 desaturase from castor (Fox et al., Proc. Natl. Acad. Sci. USA, 90:2486, 1993); .DELTA.6- and .DELTA.12-desaturases from the cyanobacteria *Synechocystis* responsible for the conversion of linoleic acid (18:2) to gamma-linolenic acid (18:3 gamma) (Reddy et al., Plant Mol. Biol., 22:293, 1993); a gene from *Arabidopsis thaliana* that encodes an omega-3 desaturase (Arondel et al., Science, 258:1353, 1992); plant .DELTA.9 desaturases (PCT Application Publ. No. WO 91/13972) and soybean and *Brassica* .DELTA.15 desaturases (European Patent Application Publication No. EP0616644).

Phytate metabolism may also be modified by introduction of a phytase-encoding gene to enhance breakdown of phytate, adding more free phosphate to the transformed plant. For example, see Van Hartingsveldt et al., (Gene, 127:87, 1993), which discloses the nucleotide sequence of an *Aspergillus niger* phytase gene. In maize, this, for example, could be accomplished by cloning and then reintroducing DNA associated with the single allele which is responsible for maize mutants characterized by low levels of phytic acid. See Raboy et al., Plant Physiol., 124:355, 1990.

A number of genes are known that may be used to alter carbohydrate metabolism. For example, plants may be transformed with a gene coding for an enzyme that alters the branching pattern of starch. See Shiroza et al., (J. Bacteriol., 170:810, 1988), which discloses the nucleotide sequence of *Streptococcus mutans* fructosyltransferase gene, Steinmetz et al., (Mol. Gen. Genet., 20:220, 1985), which discloses the nucleotide sequence of *Bacillus subtilis* levansucrase gene), Pen et al., (Biotechnology, 10:292, 1992), which discloses the production of transgenic plants that express *Bacillus licheniformis* .alpha.-amylase, Elliot et al., (Plant Molec. Biol., 21:515, 1993), which discloses the nucleotide sequences of tomato invertase genes, Sorgaard et al., (J. Biol. Chem., 268:22480, 1993), which discloses site-directed mutagenesis of barley .alpha.-amylase gene, and Fisher et al., (Plant Physiol., 102:1045, 1993) which discloses maize endosperm starch branching enzyme II. The Z10 gene encoding a 10 kD zein storage protein from maize may also be used to alter the quantities of 10 kD zein in the cells relative to other components (Kirihara et al., Gene, 71:359, 1988). U.S. Pat. No. 6,930,225 describes maize cellulose synthase genes and methods of use thereof.

Resistance to Abiotic Stress: Abiotic stress includes dehydration or other osmotic stress, salinity, high or low light intensity, high or low temperatures, submergence, exposure to heavy metals, and oxidative stress. Delta-pyrroline-5-carboxylate synthetase (P5CS) from mothbean has been used to provide protection against general osmotic stress Mannitol-1-phosphate dehydrogenase (mt1D) from *E. coli* has been used to provide protection against drought and salinity. Choline oxidase (codA from *Arthrobacter globiformis*) can protect against cold and salt. *E. coli* choline dehydrogenase (betA) provides protection against salt. Additional protection from cold can be provided by omega-3-fatty acid desaturase (fad7) from *Arabidopsis thaliana*. Trehalose-6-phosphate synthase and levan sucrase (SacB) from yeast and *Bacillus subtilis*, respectively, can provide protection against drought (summarized from Annex II Genetic Engineering for Abiotic Stress Tolerance in Plants, Consultative Group On International Agricultural Research Technical Advisory Committee). Overexpression of superoxide dismutase can be used to protect against superoxides, as described in U.S. Pat. No. 5,538,878 to Thomas et al.

Additional Traits: Additional traits can be introduced into the maize variety of the present invention. A non-limiting example of such a trait is a coding sequence which decreases RNA and/or protein levels. The decreased RNA and/or protein levels may be achieved through RNAi methods, such as those described in U.S. Pat. No. 6,506,559 to Fire et al.

Another trait that may find use with the maize variety of the invention is a sequence which allows for site-specific recombination. Examples of such sequences include the FRT sequence used with the FLP recombinase (Zhu and Sadowski, J. Biol. Chem., 270:23044, 1995); and the LOX sequence used with CRE recombinase (Sauer, Mol. Cell. Biol., 7:2087, 1987). The recombinase genes can be encoded at any location within the genome of the maize plant, and are active in the hemizygous state.

It may also be desirable to make maize plants more tolerant to or more easily transformed with *Agrobacterium tumefaciens*. Expression of p53 and iap, two baculovirus cell-death suppressor genes, inhibited tissue necrosis and DNA cleavage. Additional targets can include plant-encoded proteins that interact with the *Agrobacterium* Vir genes; enzymes involved in plant cell wall formation; and histones, histone acetyltransferases and histone deacetylases (reviewed in Gelvin, Microbiology & Mol. Biol. Reviews, 67:16, 2003).

In addition to the modification of oil, fatty acid or phytate content described above, it may additionally be beneficial to modify the amounts or levels of other compounds. For example, the amount or composition of antioxidants can be altered. See, for example, U.S. Pat. Nos. 6,787,618 and 7,154,029 and International Patent Application Publication No. WO 00/68393, which disclose the manipulation of antioxidant levels, and International Patent Application. Publication No. WO 03/082899, which discloses the manipulation of an antioxidant biosynthetic pathway.

Additionally, seed amino acid content may be manipulated. U.S. Pat. No. 5,850,016 and International Patent Application Publication No. WO 99/40209 disclose the alteration of the amino acid compositions of seeds. U.S. Pat. Nos. 6,080,913 and 6,127,600 disclose methods of increasing accumulation of essential amino acids in seeds. U.S. Pat. No. 5,559,223 describes synthetic storage proteins in which the levels of essential amino acids can be manipulated. International Patent Application Publication No. WO 99/29882 discloses methods for altering amino acid content of proteins. International Patent Application Publication No. WO 98/20133 describes proteins with enhanced levels of essential amino acids. International Patent Application Publication No. WO 98/56935 and U.S. Pat. Nos. 6,346,403, 6,441,274 and 6,664,445 disclose plant amino acid biosynthetic enzymes. International Patent Application Publication No. WO 98/45458 describes synthetic seed proteins having a higher percentage of essential amino acids than wild-type.

U.S. Pat. No. 5,633,436 discloses plants comprising a higher content of sulfur-containing amino acids; U.S. Pat. No. 5,885,801 discloses plants comprising a high threonine content; U.S. Pat. No. 5,885,802 discloses plants comprising a high methionine content; U.S. Pat. No. 5,912,414 discloses plants comprising a high methionine content; U.S. Pat. No. 5,990,389 discloses plants comprising a high lysine content; U.S. Pat. No. 6,459,019 discloses plants comprising an increased lysine and threonine content; International Patent Application Publication No. WO 98/42831 discloses plants comprising a high lysine content; International Patent Application Publication No. WO 96/01905 discloses plants comprising a high threonine content; and International Patent Application Publication No. WO 95/15392 discloses plants comprising a high lysine content.

All cited patents and patent publications referred to in this application are incorporated herein by reference in their entirety. All of the materials and methods disclosed and claimed herein can be made and used without undue experimentation as instructed by the above disclosure and illustrated by the examples. Although the materials and methods of this invention have been described in terms of embodiments and illustrative examples, it will be apparent to those of skill in the art that substitutions and variations can be applied to the materials and methods described herein without departing from the concept, spirit, and scope of the invention. All such similar substitutes and modifications apparent to those skilled in the art are deemed to be within the spirit, scope, and concept of the invention as encompassed by the embodiments of the inventions recited herein and the specification and appended claims.

What is claimed is:

1. A maize plant of the maize variety designated ICH19849, wherein representative seed of the maize variety ICH19849 has been deposited under ATCC Accession number PTA-126949.

2. The maize plant of claim 1, which is grown from seed that has been deposited under ATCC Accession number PTA-126949.

3. A maize plant having all the physiological and morphological characteristics of the plant of claim 1.

4. The maize plant of claim 1, further comprising in its genome a transgene introduced by stable transformation.

5. A seed that produces the maize plant of claim 1.

6. A composition comprising the seed of claim 5 and a growth medium.

7. The composition of claim 6, wherein the growth medium is soil or a synthetic medium.

8. A plant part of the maize plant of claim 1, wherein the plant part is a pollen grain, a silk, a tassel, an anther, an ovule, meristem, root, leaf, shoot, or shoot apex.

9. A protoplast, cell, tissue culture, or callus from the maize plant of claim 1.

10. A maize plantlet or plant regenerated from the cell, tissue culture, or callus of claim 9, where the maize plantlet or plant has all of the physiological and morphological characteristics of the maize plant of claim 1.

11. A seed of maize variety ICH19849, wherein representative seed of the maize variety ICH19849 has been deposited under ATCC Accession number PTA-126949.

12. A method of producing maize seed, comprising cultivating the maize plant of claim 1 and harvesting seed from the plant.

13. A method of producing a commodity maize product, the method comprising obtaining the maize plant of claim 1 or a part of the plant, and producing the commodity maize product therefrom.

14. The maize plant of claim 1, wherein the maize plant has at least one additional trait introduced using at least one process selected from the group consisting of transformation, genome editing, epigenetic modification, and mutagenesis, and where the maize plant has all of the physiological and morphological characteristics of the maize plant of claim 1 in addition to the at least one additional trait.

15. The maize plant of claim 14, wherein the at least one process comprises use of at least one agent selected from the group consisting of: a bacterium capable of transforming a plant cell; a particle or nanoparticle; a recombinant DNA vector; and a nuclease, or a fusion protein or protein complex including a nuclease, and optionally polynucleotides associated with the nuclease.

16. The maize plant of claim 1, wherein the maize plant has at least one additional trait associated with a transgene that is introduced into by backcrossing or genetic transformation of a maize plant designated ICH19849, and where the maize plant has all of the physiological and morphological characteristics of the maize plant of claim 1 in addition to the at least one additional trait.

17. A method of producing a progeny maize seed derived from maize variety ICH19849, comprising harvesting seed of a progeny maize plant obtained by crossing the maize plant of claim 1 with itself or with a second maize plant, thereby producing progeny maize seed.

* * * * *